United States Patent [19]

Janoff et al.

[11] Patent Number: 5,041,278

[45] Date of Patent: Aug. 20, 1991

[54] ALPHA TOCOPHEROL-BASED VESICLES

[75] Inventors: Andrew S. Janoff, Yardley, Pa.; Lois E. Bolcsak, Lawrenceville; Alan L. Weiner, both of Lawrenceville, N.J.; Paul A. Tremblay, Hamilton, N.J.; Michael V. W. Bergamini, Easton, Pa.

[73] Assignee: The Liposome Company, Inc., Princeton, N.J.

[21] Appl. No.: 280,551

[22] Filed: Dec. 6, 1988

Related U.S. Application Data

[60] Division of Ser. No. 911,138, Sep. 24, 1986, Pat. No. 4,861,580, and a continuation-in-part of Ser. No. 786,740, Oct. 15, 1985, abandoned.

[51] Int. Cl.$^5$ ............... A61K 9/139; A61K 9/133; A61K 31/355; A61K 43/00
[52] U.S. Cl. ................... 424/1.1; 264/4.1; 264/4.6; 424/7.1; 424/450; 428/402.2; 436/829; 514/458; 514/885; 514/913
[58] Field of Search ............ 264/4.1, 4.6; 424/1.1, 424/450, 7.1; 428/402.2; 436/829; 549/410; 514/913, 458

[56] References Cited

U.S. PATENT DOCUMENTS

| | | | |
|---|---|---|---|
| 3,136,695 | 6/1964 | Tansey | 252/315.4 X |
| 3,993,754 | 11/1976 | Rahman et al. | 424/450 X |
| 4,145,410 | 3/1979 | Sears | 514/789 X |
| 4,193,983 | 3/1980 | Ullman et al. | 424/12 |
| 4,224,179 | 9/1980 | Schneider | 264/4.6 |
| 4,235,871 | 11/1980 | Papahadjopoulos et al. | 424/450 |
| 4,271,196 | 6/1981 | Schmidt | 514/786 |
| 4,342,739 | 8/1982 | Kakimi et al. | 424/1.1 |
| 4,376,118 | 3/1983 | Daher et al. | 514/153 |
| 4,411,894 | 10/1983 | Schrank et al. | 514/777 X |
| 4,438,052 | 3/1984 | Weder et al. | 264/4.6 |
| 4,522,803 | 6/1985 | Lenk et al. | 424/1.1 |
| 4,698,359 | 10/1987 | Niederer et al. | 514/966 X |
| 4,721,612 | 1/1988 | Janoff et al. | 424/1.1 |
| 4,861,580 | 8/1989 | Janoff et al. | 424/1.1 |

FOREIGN PATENT DOCUMENTS

| | | |
|---|---|---|
| 0036676 | 9/1981 | European Pat. Off. |
| 0055576 | 7/1982 | European Pat. Off. |
| 2438481 | 5/1980 | France |
| 1593127 | 7/1978 | United Kingdom |
| WO85/00968 | 3/1985 | World Int. Prop. O. |
| WO85/04578 | 10/1985 | World Int. Prop. O. |
| WO86/00238 | 1/1986 | World Int. Prop. O. |
| WO86/01102 | 2/1986 | World Int. Prop. O. |
| WO86/01103 | 2/1986 | World Int. Prop. O. |
| WO86/05977 | 10/1986 | World Int. Prop. O. |

OTHER PUBLICATIONS

Lai et al., "Thermotropic Behavior of Aqueous Dispersions of Phospholipid Cholesterylhemisuccinate and Phospholipid-Tocopherol Hemisuccinate Mixtures", Biophysicial Journal, Abstracts, vol. 45, No. 2, part 2, p. 192a, Feb. 19–23, 1984.

Bangham et al., "Diffusion of Univalent Ions Across the Lamellae of Swollen Phospholipids", J. Mol. Biol. 13:228 (1965).

Brockerhoff et al., "Preparation and Structural Studies of Cholesterol Bilayers", Biochim. Biophys. Acta., 691:227 (1982).

Deamer et al., "Liposome Preparation: Methods and Mechanisms", (1983), In: Liposomes, ed. M. Ostro, Marcel Dekker Inc., N.Y., pp. 27–51.

(List continued on next page.)

Primary Examiner—Richard D. Lovering
Attorney, Agent, or Firm—Allen Bloom; Catherine Kurtz; Ilene Janofsky

[57] ABSTRACT

Methods and compositions are described for the preparation of alpha-tocopherol vesicles, the bilayers of which comprise a salt form of an organic acid derivative of alpha-tocopherol such as the Tris salt form of alpha-tocopherol hemisuccinate. The method is rapid and efficient and does not require the use of organic solvents. The alpha-tocopherol vesicles may be used to entrap compounds which are insoluble in aqueous solutions. Such preparations are especially useful for entrapping bioactive agents of limited solubility, thus enabling administration in vivo.

95 Claims, 4 Drawing Sheets

LEGEND
A = CYCLOSPORIN A
B = ALPHA-TOCOPHEROL HEMISUCCINATE
C = CHOLESTEROL HEMISUCCINATE
• = ACCEPTABLE
+ = UNACCEPTABLE

OTHER PUBLICATIONS

Gregoriadis, "The Carrier Potential of Liposomes in Biology and Medicine", The New England J. of Medicine, (1976), 295:13, 704–710.

Hansrani et al., "The Preparation and Properties of Sterile Intravenous Emulsions", (1983), J. Parenteral Sci. Tech., 37:4, 145–150.

Hunt et al., "Alpha-Tocopherol Retards Autoxidation and Prolongs the Shelf-Life of Liposomes", (1981), Int. J. Pharm., 8:101–110.

Lai et al., "Effects of Replacement of the Hydroxyl Group of Cholesterol and Tocopherol on the Thermotropic Behavior of Phospholipid Membranes", (1985), Biochem., 24, 1646–1653.

Lundmark et al., "Soya Sterols: Functional Plant-Derived Ingredients for Toiletries—Part I", (1976), Soap/Cosmetics/Chemical Specialties, 52:33–40.

Massey et al., "Interaction of Vitamin E with Saturated Phospholipid Bilayers", (1982), Biochem. Biophys. Res. Comm. 106:3, 842–847.

Myers et al., "Adriamycin:Amelioration of Toxicity by Alpha-Tocopherol", (1976), Cancel Treatment Reports, 60:7, 961–962.

Papahadjopoulos et al., "Phospolipid Model Membranes I. Structural Characteristics of Hydrated Liquid Crystals", (1967), Biochim. Biophys. Acta., 135:624–638.

Sessa et al., "Incorporation of Lysozyme into Liposomes", (1970), J. Biol. Chem., 245:3295.

*Hackh's Chemical Dictionary*, 4th Edition, Completely Revised and Edited by J. Grant, McGraw-Hill Book Co., 1969, p. 698.

Gregoriadis: "The Carrier Potential of Liposomes in Biology & Medicine (first of two parts)", *The New England Journal of Medicine,* 295:13, 1976, pp. 704–710.

Lai et al., "Effects of Replacement of the Hydroxyl Group of Cholesterol and Tocopherol on the Thermotropic Behavior of Phospholipid Membranes", *Biochemistry* 1985, 24: pp. 1646–1653.

U.S. patent application Ser. No. 773,429, filing date 9/10/85, name, Janoff, et al., status pending.

U.S. patent application Ser. No. 360,964, filing date 6/26/89, name, Janoff, et al., status pending.

U.S. patent application Ser. No. 284,751, filing date 12/12/88, name, Bally, et al., status pending.

U.S. patent application Ser. No. 759,419, filing date 7/26/85, name, Janoff, et al., status pending.

U.S. patent application Ser. No. 749,161, filing date 6/26/85, name, Bally, et al., status abandoned.

U.S. patent application Ser. No. 638,809, filing date 8/08/84, name, Janoff, et al., status abandoned.

U.S. patent application Ser. No. 310,495, filing date 2/13/89, name, Cullis, et al., status pending.

U.S. patent application Ser. No. 788,017, filing date 10/16/85, name, Cullis, et al., status abandoned.

U.S. patent application Ser. No. 622,690, filing date 6/20/84, name, Cullis, et al., status abandoned.

U.S. patent application Ser. No. 4,762, filing date 1/07/87, name, Cullis et al., status pending.

U.S. patent application Ser. No. 622,502, filing date 6/20/84, name, Cullis, et al., status abandoned.

LEGEND

A = CYCLOSPORIN A
B = ALPHA-TOCOPHEROL HEMISUCCINATE
C = CHOLESTEROL HEMISUCCINATE
● = NO CRYSTALS PRESENT
+ = CRYSTALS PRESENT

LEGEND

A = CYCLOSPORIN A
B = ALPHA-TOCOPHEROL HEMISUCCINATE
C = CHOLESTEROL HEMISUCCINATE
● = ACCEPTABLE
+ = UNACCEPTABLE

LEGEND a = MICONAZOLE
b = CHOLESTEROL HEMISUCCINATE (CHS)
c = ALPHA-TOCOPHEROL HEMISUCCINATE (THS)
● = ACCEPTABLE
+ = UNACCEPTABLE

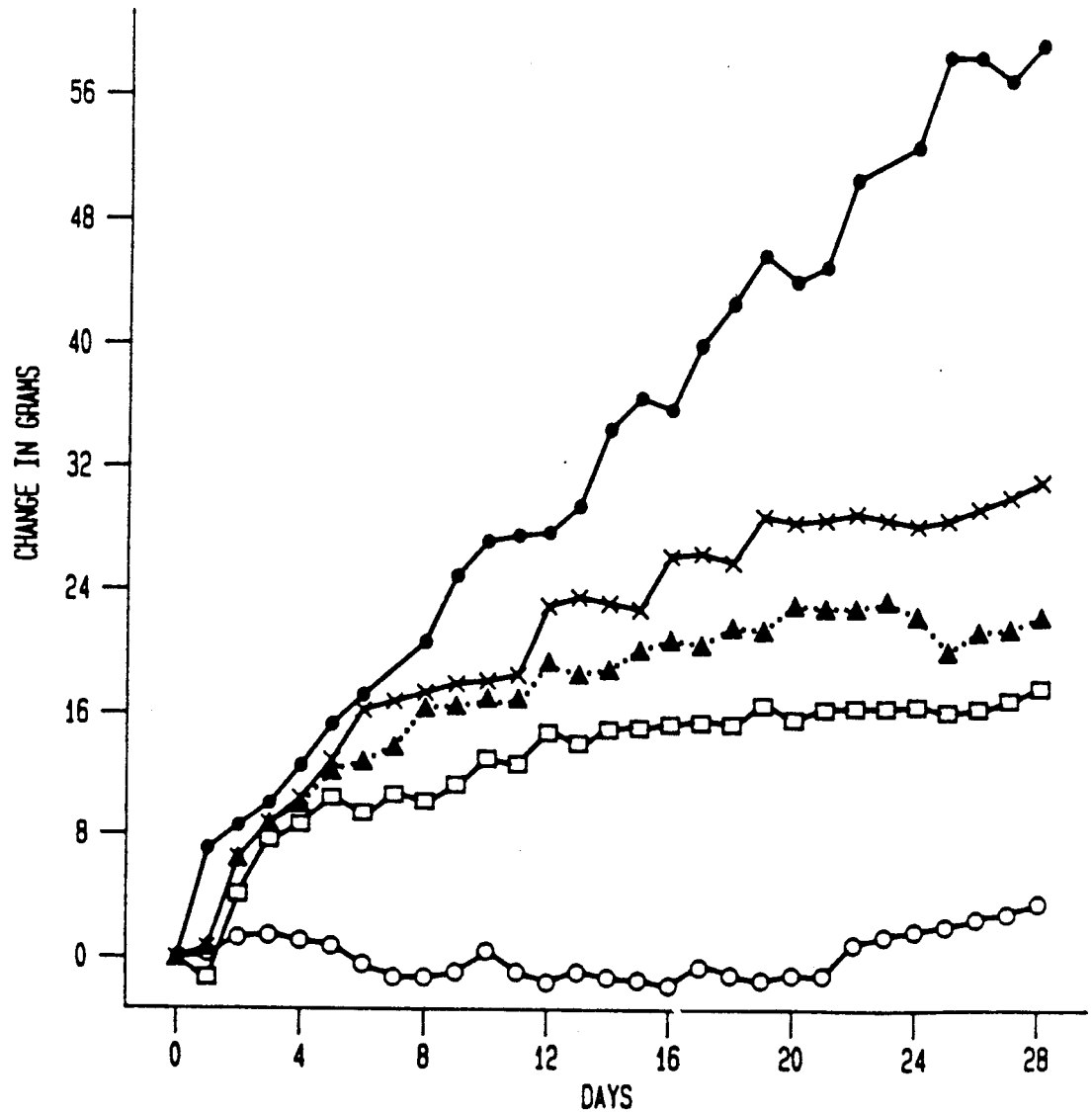

ALPHA TOCOPHEROL-BASED VESICLES

RELATED COPENDING APPLICATIONS

This application is a division of copending application Ser. No. 911,138, filed Sept. 24, 1986, now U.S. Pat. No. 4,861,580 and a continuation-in-part of copending application Ser. No. 786,740, filed Oct. 15, 1985 and now abandoned.

BACKGROUND OF THE INVENTION

The present invention relates to the methods and compositions for the entrapment of compounds in vesicles composed of salt forms of organic acid derivatives of alpha-tocopherol (Vitamin E) that are capable of forming bilayers.

Alpha-tocopherol, to which a hydrophilic moiety such as a salt form of an organic acid is attached, can be used to prepare suspensions of multilamellar or small unilamellar vesicles. These vesicles may be prepared with or without the use of organic solvents, and they may entrap, or associate with, water-soluble compounds, partially water-soluble compounds and water-insoluble compounds. For convenience, the vesicles of the invention will simply be referred to as "alpha-tocopherol vesicles", but it must be understood that salt forms of organic acid derivatives of alpha-tocopherol are always used in the preparation of the vesicles.

The alpha-tocopherol vesicles described herein are particularly useful for the entrapment of, or association with, biologically active compounds or pharmaceutical compounds which can be administered in vivo. Alternatively the vesicles of the present invention may be used in vitro. For instance, the alpha-tocopherol hemisuccinate vesicles described herein may be used in vitro in divalent cation-dependent assay systems.

The alpha-tocopherol vesicles of the invention are liposomes. Liposomes are completely closed bilayer membranes containing an encapsulated aqueous phase. Liposomes may be any variety of multilamellar vesicles (onion-like structures characterized by membrane bilayers each separated by an aqueous layer) or unilamellar vesicles (possessing a single membrane bilayer).

Two parameters of liposome preparations are functions of vesicle size and lipid concentration: (1) Captured volume, defined as the volume enclosed by a given amount of lipid, is expressed as units of liters entrapped per mole of total lipid (1 mol$^{-1}$). The captured volume depends upon the number of lamellae and the radius of the liposomes, which in turn is affected by the lipid composition of the vesicles and the ionic composition of the medium. (2) Encapsulation efficiency is defined as the fraction of the initial aqueous phase sequestered by the bilayers. (See Deamer and Uster, 1983, Liposome Preparation: Methods and Mechanisms, in Liposomes, ed. M. Ostro, Marcel Dekker, Inc. N.Y., pp. 27–51.

The original method for liposome preparation [Bangham et al., J. Mol. Biol. 13:228 (1965)] involved suspending phospholipids in an organic solvent which was then evaporated to dryness, leaving a waxy deposit of phospholipid on the reaction vessel. Then an appropriate amount of aqueous phase was added, the mixture was allowed to "swell", and the resulting liposomes which consisted of multilamellar vesicles (hereinafter referred to as MLVs) were dispersed by mechanical means. The structure of the resulting membrane bilayer is such that the hydrophobic (non-polar) "tails" of the lipid orient toward the center of the bilayer, while the hydrophilic (polar) "heads" orient toward the aqueous phase. This technique provided the basis for the development of the small sonicated unilamellar vesicles (hereinafter referred to as SUVs) described by Papahadjopoulos and Miller [Biochim. Biophys. Acta. 135:624 (1967)].

An effort to increase the encapsulation efficiency involved first forming liposome precursors or micelles, i.e., vesicles containing an aqueous phase surrounded by a monolayer of lipid molecules oriented so that the polar head groups are directed toward the aqueous phase. Liposome precursors are formed by adding the aqueous solution to be encapsulated to a solution of polar lipid in an organic solvent and sonicating. The liposome precursors are then emulsified in a second aqueous phase in the presence of excess lipid and evaporated. The resultant liposomes, consisting of an aqueous phase encapsulated by a lipid bilayer are dispersed in aqueous phase (see U.S. Pat. No. 4,224,179 issued Sept. 23, 1980 to M. Schneider).

In another attempt to maximize the encapsulation efficiency, Paphadjapoulos (U.S. Pat. No. 4,235,871 issued Nov. 25, 1980) describes a "reverse-phase evaporation process" for making oligolamellar lipid vesicles also known as reverse-phase evaporation vesicles (hereinafter referred to as REVs). According to this procedure, the aqueous material to be encapsulated is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles (large unilamellar vesicles, or LUVs) and some oligolamellar vesicles which are characterized by only a few concentric bilayers with a large internal aqueous space.

Liposomes can also be prepared in the form of: (a) stable plurilamellar vesicles (SPLVs) according to the procedures set forth in Lenk et. al., U.S. Pat. No. 4,522,803, (b) monophasic vesicles (MPVs) according to the procedures of Lenk et. al., U.S. Pat. No. 4,588,578 and (c) freeze and thawed multilamellar vesicles (FATMLVs) according to the procedures of Bally et. al., U.S. patent application Ser. No. 800,545, filed Nov. 21, 1985 and now abandoned Relevant portions of the cited applications and patent in this paragraph are incorporated herein by reference.

Liposomes can be dehydrated and rehydrated; see Janoff et al, "Dehydrated Liposomes,", PCT application Ser. No. 8601103, published Feb. 27, 1986, revelent portions of which are incorporated herein by reference.

Much has been written regarding the possibilities of using liposomes for drug delivery systems. See, for example, the disclosures in U.S. Pat. No. 3,993,754 issued on Nov. 23, 1976, to Yueh-Erh Rahman and Elizabeth A. Cerny and U.S. Pat. No. 4,145,410 issued on Mar. 20, 1979, to Barry D. Sears. In a liposome drug delivery system the medicament is entrapped during liposome formation and then administered to the patient to be treated. The medicament may be soluble in water or in a non-polar solvent. Typical of such disclosures are U.S. Pat. No. 4,235,871 issued Nov. 25, 1980, to Papahadjapoulos and Szoka and U.S. Pat. No. 4,224,179, issued Sept. 23, 1980 to M. Schneider. When preparing liposomes for use in vivo it would be advantageous (1) to eliminate the necessity of using organic solvents during the preparation of liposomes; and (2) to maximize the encapsulation efficiency and captured volume so that a greater volume and concentration of the entrapped material can be delivered per dose.

SUMMARY OF THE INVENTION

The present invention involves methods and compositions for the entrapment and administration of various compounds in vesicles, the bilayers of which comprise salt forms of organic acid derivatives of alpha-tocopherol. The vesicles of the present invention are particularly useful for the administration of the entrapped compound in vivo, in which a case a biocompatible salt form of an organic acid derivative of D-alpha-tocopherol should be used to prepare the vesicles. In fact for in vivo administration, the tris(hydroxymethyl) aminomethane salt (tris-salt) form of organic acid derivatives of alpha-tocopherol are particularly useful as the vesicle bilayer component. Such derivatives may be the ester or hemiester of succinic acid, and the vesicles may entrap bioactive agents such as but not limited to hormones, antifungal agents and antiglaucoma agents. The vesicles may be administered by various routes including, but not limited to, topically, parenterally, orally and vaginally.

The method for preparing the alpha-tocopherol vesicles involves adding to an aqueous buffer a salt form of an organic acid derivative of alpha-tocopherol capable of forming closed bilayers in an amount sufficient to form completely closed bilayers which entrap an aqueous compartment. A suspension of vesicles is formed by shaking the mixture. The formation of vesicles is facilitated if the aqueous buffer also contains the counterion of the salt in solution. Furthermore, if the dissociated salt form of the organic acid derivative of alpha-tocopherol is negatively charged at neutral pH, the aqueous buffer should be essentially free of divalent cations. Similarly, when the dissociated salt form of the organic acid derivative of alpha-tocopherol is positively charged at neutral pH, the aqueous buffer should be essentially free of multivalent anions. The application of energy of the suspension, e.g., sonication, will convert multilamellar vesicles to unilamellar vesicles.

To entrap a water-soluble compound, a partially water-soluble compound or a water-insoluble compound in the alpha-tocopherol vesicles of the present invention, a number of approaches are possible. Compounds which either partition into the alpha-tocopherol bilayers (e.g., water-insoluble compounds) or water-soluble compounds may be added to the aqueous phase before formation of the vesicles to entrap the agent within the vesicles during formation. Alternatively, compounds which are water-insoluble or lipid soluble may be added to the suspension of vesicles after the vesicles are formed, in which case the compound partitions into the alpha-tocopherol bilayers. In another embodiment, a water-insoluble compound and the salt-form of an organic acid derivative of alpha-tocopherol may be added to an organic solvent so that both are solubilized (co-solubilized). The organic solvent may then be evaporated, leaving a film containing a homogeneous distribution of the water-insoluble compound and the alpha-tocopherol derivative. Alpha-tocopherol vesicles entrapping the water-insoluble compounds are formed when an aqueous buffer is added to the film with agitation. Such vesicles may then be sonicated, forming unilamellar vesicles.

The alpha-tocopherol vesicles of the present invention are particularly advantageous when used to entrap water-insoluble bioactive agents or those that are sparingly soluble in water. This enables the administration in vivo of water-insoluble bioactive agents such as drugs. Furthermore, it allows for the administration in vivo of higher concentrations of the water-insoluble compounds, because it allows alteration of the dose:volume ratio. The alpha-tocopherol vesicles of the present invention offer similar advantages when used to entrap water-soluble bioactive agents. The alpha-tocopherol vesicles may be derivatized forming esters or hemiesters or organic acids, and these organic acid derivatives may further be salt forms of bioactive agents, as with pilocarpine. The vesicles of the present invention may also be used in diagnostic assays in vitro.

The present invention includes compositions comprising salt forms of organic acid derivatives of alpha-tocopherol, particularly those including bioactive agents. The salt form can be derived from an ionizable bioactive agent. In the case of pilocarpine alpha-tocopherol vesicles, the pilocarpine salt form of the organic acid derivative of alpha-tocopherol is used; preferably in a mole ratio of 1:1.

Also embraced by the present invention are compositions comprising a salt form of an organic acid derivative of a sterol and a salt form of an organic acid derivative of alpha-tocopherol. The composition can additionally contain a bioactive agent. The salt form of the organic acid derivative of either the sterol or alpha-tocopherol, or both can include an ionizable bioactive agent. Such bioactive agents include, but are not limited to, polypeptides such as the immunosuppressive agent cyclosporin A. These compositions can be used to form liposome vesicles.

The present invention affords a number of advantages in that the alpha-tocopherol vesicles:
(1) are formed easily and rapidly;
(2) have high encapsulation efficiencies compared to phospholipid MLVs;
(3) do not require the use of organic solvents for their preparation (although the alpha-tocopherol vesicles of the present invention can be prepared using organic solvents);
(4) have high captured volumes; and
(5) can entrap a bioactive or pharmaceutical agent which, when administered in vivo, is released and metabolized. The fate of the entrapped agent in vivo, depends upon the mode of administration.

The alpha-tocopherol vesicles of the present invention may further be used in a two-step process in which a material to be entrapped is first solubilized by incorporation into alpha-tocopherol vesicles, and then the alpha-tocopherol vesicles containing the entrapped material are themselves incorporated into conventional liposomes.

BRIEF DESCRIPTION OF THE DRAWINGS

The present invention may be more readily understood by reference to the following figures, wherein

FIG. 4 is a graphical representation of the effects of free and vesicle-entrapped bovine growth hormone on the growth of hypophysectomized rats, with growth measured as a change in weight shown as a function of time.

DETAILED DESCRIPTION OF THE INVENTION

Figure 1:
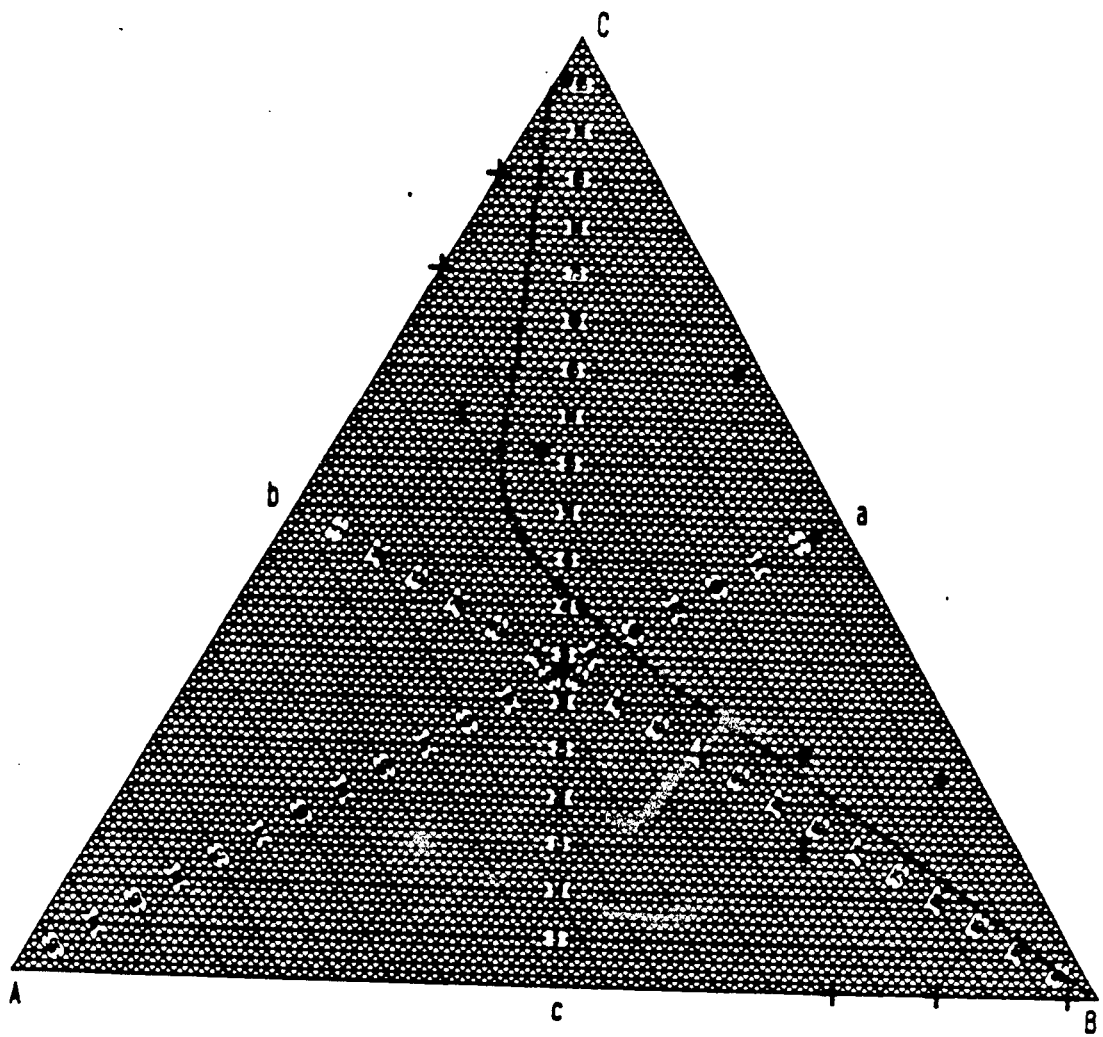
FIGS. 1 and 2 are graphical representations of the effects of constituent concentrations on the formation of complex vesicles containing alpha-tocopherol hemisuccinate Tris salt, cholesterol hemisuccinate Tris salt and associated cyclosporin and 70° C. and 60° C., respectively.

Alpha-tocopherol vesicles can be used for the entrapment of water-soluble, partially water-soluble or water-insoluble compounds in the vesicles, the bilayers of which comprise salt forms of organic acid derivatives of alpha-tocopherol that are capable of forming closed bilayers. Accordingly, the alpha-tocopherol vesicles of the present invention can be prepared to (1) entrap a water-soluble compound in the aqueous compartment; (2) entrap a water-insoluble compound which partitions into the vesicle bilayers; or (3) entrap both a water-soluble vesicle and a water-insoluble compound in one vesicle preparation.

Any salt form of an organic acid derivative of alpha-tocopherol which is capable of forming completely closed bilayers in aqueous solutions similar to liposomes may be used in the practice of the invention. The suitability of a particular salt-form of an organic acid derivative of alpha-tocopherol depends upon its ability to sequester a water-soluble compound so that the compound is not in contact with the outside environment.

To determine definitively that entrapment within the aqueous compartment of a vesicle has occurred, the following criteria for liposomes, which may be applied by analogy, have been established [See Sessa and Weissmann, Biol, Chem. 245:3295 (1970)]: (a) there must be a clear separation of free from sequestered compound by gel filtration; (b) there must be no hydrophobic or charge-charge interaction between the outermost vesicle bilayer and the entrapped compound since this may result in a failure to achieve separation of the free compound from the vesicles by molecular sieving, thereby artificially increasing the apparent sequestration efficiency. To eliminate this possibility it must be shown that the water-soluble compound added to a suspension of previously formed vesicles does not coelute with the vesicles; (c) disruption of gel-filtered vesicles by use of detergents or other membrane perturbants must induce a shift in the gel filtration pattern of the sequestered molecule from a position coincident with the vesicle peak to one that coelutes with the free molecule.

Organic acids which can be used to derivatize the alpha-tocopherol include but are not limited to the carboxylic acids, dicarboxylic acids, polycarboxylic acids, hydroxy acids, amino acids and polyamino acids. Such derivatives may be esters or hemiesters. Because the salt forms increase the water solubility of organic acids, any organic acid may be used to derivatize the alpha-tocopherol; however an advantage may be obtained if the organic acid moiety itself is water soluble. Such water-soluble organic acid moieties include but are not limited to water-soluble aliphatic carboxylic acids such as acetic, propionic, butyric, valeric acids an the like (N.B., up to four-carbon acids are miscible with water; the five-carbon free acid is partly soluble and the longer chain free acids are virtually insoluble); water-soluble aliphatic dicarboxylic acids such as malonic, succinic, glutaric, adipic, pimelic, maleic and the like (N.B., the shorter chains are appreciably m ore soluble in water; borderline solubility in water occurs at $C_6$ to $C_7$); and water-soluble aromatic dicarboxylic acids such as hemimellitic, trimesic, succinimide, and the like; polycarboxylic acids; water-soluble hydroxy acids such as glycolic, lactic, mandelic, glyceric, malic, tartaric, citric, and the like (N.B., alpha-hydroxy acids containing a branched chain attached to the alpha-carbon of the carbonyl group would be less susceptible to hydrolysis and, therefore, advantageous in the practice of the present invention); and any of the amino acids and polyamino acids.

The salt forms of the derivatized alpha-tocopherol can be prepared by dissolving both the organic acid derivative of the alpha-tocopherol and the counterion of the salt (e.g., the free base of the salt) in an appropriate volatile solvent, and removing the solvent by evaporation or a similar technique leaving a residue which consists of the salt form of the organic acid derivative of alpha-tocopherol. Counterions that may be used include, but are not limited to, tris, 2-amino-2-methyl-1-3-propanediol, 2-aminoethanol, bis-tris propane, triethanolamine, and the like to form the corresponding salt. In fact, the free base of an ionizable bioactive agent such as miconazole free base and the like may be used as the counterion.

Generally a 1:1 molar ratio of the free base of the bioactive agent and the dicarboxylic acid derivative of alpha-tocopherol are employed to prepare the corresponding bioactive agent salt form. An organic solvent which dissolves both starting materials are those such as methanol, ethanol, chloroform, methylene chloride, dimethylformamide and dimethysulfoxide. The starting materials are added to the solvent, preferably at about 20–50° C., more preferably about 20–30° C. Following reaction, the resulting bioactive agent salt can be isolated by solvent removal under reduced pressure, evaporation, crystalization, or other methods known in the art. The preferred dicarboxylic acid derivative is that of succinic acid. The preferred alpha-tocopherol is D-alpha-tocopherol.

When the bioactive agent free base is pilocarpine and the dicarboxylic acid is succinic acid, mole ratios ranging from 1:0.5 to 1:1 pilocarpine:D-alpha-tocopherol may be used; most preferably equi-molar amounts of the starting materials are dissolved in a polar organic solvent such as chloroform or methylene chloride. For methylene chloride, the starting materials are preferably added at about 30–60° C., more preferably about 40–60° C., most preferably about 55° C., and heated to reflux. After reaction is complete, the solvent is removed under reduced pressure to obtain the product which is the pilocarpine salt of alpha-tocopherol hemisuccinate.

The free base of antifungal agents such as miconazole, terconazole, econazole, isoconazole, tioconazole, bifonazole, clotrimazole, ketoconazole, butaconazole, itraconazole, oxiconazole, fenticonazole, nystatin, naftifine, amophotericin B, zinoconazole and ciclopirox olamine, preferably miconazole or terconazole ay be employed as the ionizable bioactive agent.

The alpha-tocopherol vesicles of the present invention may be prepared by adding to an aqueous phase a salt form of an organic acid derivative of alpha-tocopherol so that the derivatized alpha-tocopherol is present in an amount sufficient to form vesicles (i.e., completely closed bilayers containing an entrapped aqueous compartment). The preparation is then shaken until a milky suspension of vesicles, generally multilamellar, is formed. In the preferred embodiment, the aqueous phase should contain the sat in solution to facilitate vesicle formation. Furthermore, if the dissociated salt form of the organic acid derivative of the alpha-tocopherol is negatively charged at neutral pH, the aqueous buffer should be essentially free of multivalent cations. Similarly, when the dissociated salt form of the organic acid derivative is positively charged at neutral pH, the aqueous buffer should be essentially free of multivalent anions.

The vesicles of the invention may be used as multilamellar vesicles, or size-reduced using a number of techniques known in the art, such as filtration or sonication. Vesicles may also be size reduced using the VET procedure (vesicle extrusion technique) as described in Hope et al., BBA Vol. 812, 1985, pp. 55-65, and in copending U.S. patent application Ser. No. 788,017, Cullis et al., entitled "Extrusion Technique for Producing Unilamellar Vesicles", filed Oct. 16, 1985 and now abandoned. Another technique for sizing vesicles is the CSR procedure (continuous size reduction) whereby vesicles are continuously extruded through a filter unit by a pump.

In complete contrast to reported methods for multilamellar vesicle formation [e.g., phospholipid vesicles or the cholesterol liposomes of Brockerhoff and Ramsammy, Biochim. Biophys. Acta. 691:227 (1982)], the method for the formation of the alpha-tocopherol multilamellar vesicles of the present invention does not require the use of organic solvents. Furthermore, unlike the method of Brockerhoff and Ramsammy sonication is not necessary to form multilamellar vesicles. Sonication of the milky suspension of the alpha-tocopherol multilamellar vesicles of the present invention, or the use of a French press (SLM-Aminco, Urbana, Ill.) followed by sonication, may be used however to convert the milky suspension of multilamellar alpha-tocopherol vesicles to a clear suspension of unilamellar vesicles. Often, use of the French press without sonication results in unilamellar vesicles.

As previously explained, the tris-salt form of any organic acid derivative of alpha-tocopherol may be advantageously used in the practice of the present invention. For example, the tris-salt form of an alpha-tocopherol hemi-dicarboxylic acid such as an alpha-tocopherol hemisuccinate or a mixture of hemisuccinates are particularly useful for forming the vesicle bilayers of the alpha-tocopherol vesicles to be administered in vivo. For instance, when using alpha-tocopherol hemisuccinate, about 5 to 700 micromoles of the tris-salt form may be added to about 5.0 ml of aqueous buffer containing Tris-HCl (tris(hydroxymethyl)-aminomethane hydrochloride) to form vesicles. In this case, the aqueous buffer should be essentially free of divalent cations.

According to the present invention, the entrapment or association of water-soluble compounds, water-insoluble compounds, or sparingly soluble compounds in liposomes composed of the salt form of organic acid derivatives of alpha-tocopherol may be accomplished in a number of ways:

(1) A water-insoluble compound can be added to a suspension of alpha-tocopherol vesicles (either multilamellar or unilamellar), which were prepared as described above using an appropriate salt form of an organic acid derivative of alpha-tocopherol. The compound is entrapped in the vesicles because it partitions into the alpha-tocopherol bilayers. This embodiment may be conveniently carried out as follows: the water-insoluble compound may be dissolved in an appropriate organic solvent which is then evaporated, leaving a film or residue of the compound. When an aqueous suspension of previously formed alpha-tocopherol vesicles is added to the residue, the residue will be entrapped in the bilayers of the vesicles. In the preferred embodiment unilamellar vesicles should be used. If multilamellar vesicles are used instead, the water-insoluble compound may be entrapped only in the outermost bilayers of the vesicles, leaving the innermost bilayers unaltered with a wasteful use of derivatized alpha-tocopherol.

(2) Both a water-insoluble compound and the salt form of an organic acid derivative of alpha-tocopherol can be co-solubilized in an organic solvent which is then evaporated, leaving a film comprising a homogeneous distribution of the water-insoluble compound and the alpha-tocopherol derivative. A suspension of alpha-tocopherol vesicles containing the entrapped compound is formed when an aqueous phase is added to the film with shaking. Multilamellar vesicles may be converted to unilamellar vesicles as previously described.

(3) A water-soluble compound or a water-insoluble compound can be entrapped in the alpha-tocopherol vesicles by adding the compound to the aqueous phase which is used in the preparation of the vesicles; i.e., the compound can be added to the aqueous phase before or simultaneously with the addition of the salt form of an organic acid derivative of alpha-tocopherol. In this case, a water-insoluble compound becomes entrapped when it partitions into the bilayers during vesicles formation; whereas a water-soluble compound becomes entrapped in the aqueous compartment of the vesicles. In either case, the multilamellar vesicles can be converted to unilamellar vesicles as previously described.

(4) If the bioactive agent is ionizable, the free base of the bioactive agent may be used as the counterion to prepare the salt form of the organic acid derivative of alpha-tocopherol. The resulting composition can have enhanced solubility or stability. Furthermore, the alpha-tocopherol vesicles may be prepared by any of the methods previously described herein using the bioactive agent-salt form of the organic acid derivative of alpha-tocopherol. For example, the free base of antifungal agents such as miconazole, terconazole, econazole, isoconazole, tioconazole, bifonazole, clotrimazole, ketoconazole, butaconazole, itraconazole, oxiconazole, fenticonazole, nystatin, naftifine, amphotericine B, zinoconazole and ciclopirox olamine, preferably miconazole or terconazole, may be used to make the salt derivatives in one embodiment of the present invention. Also, the free base of pilocarpine may be used to make the salt derivatives in one embodiment of the present invention. Liposomes using the pilocarpine salt derivative of alpha-tocopherol hemisuccinate may be made by adding an aqueous solution to the dried salt form of the pilocarpine alpha-tocopherol hemisuccinate at a temperature of 30-40° C. and agitating the suspension.

Examples of aqueous solutions that may be used are water for injection, USP; and any of the following alone or in combination: 0.1% (w/v) benzylkonium chloride, 0.025–0.1% (w/v) sorbic acid EDTA (ethylenediaminetetraacetic acid), 1.4% (w/v) polyvinyl alcohol, 0.1% (w/v) benzylkonium chloride, and 0.05–0.50% (w/v) hydroxypropyl methylcellulose. Other ionizable bioactive agents named herein may also be employed.

The compositions of the present invention, in addition to salt forms of organic acid derivatives of alpha-tocopherol, may contain bioactive agents entrapped within or between the bilayers of the vesicle, or alternatively the bioactive agent may be in association with the bilayers. Such an association may result in the bioactive agent being located on the exterior of the vesicle.

The compositions of the present invention may be used for ocular administration in the treatment of ocular afflictions such as glaucoma. In such applications the compositions may be administered by ocular delivery systems known in the art such as eye droppers or applicators. The compositions can further contain mucomimetics such as hyaluronic acid, chondroitin sulfate, hydroxypropyl methylcellulose, or polyvinyl alcohol; and preservations, such as sorbic acid EDTA or benzylkonium chloride, in the above-named percentages, and the usual quantities of diluents and/or carrier materials.

For administration to humans in the treatment of ocular afflictions such as glaucoma, the prescribing physician will ultimately determine the appropriate dose for a given human subject, and this can be expected to vary according to the age, weight, and response to the individual as well as the nature and severity of the patient's symptoms. Typically, ocular dosages of the compositions will be in the range of 25–50 ul of a 4% pilocarpine solution administered 1–2 times daily for an average adult patient in a suitable pharmaceutically acceptable diluent or carrier. These figures are illustrative only, however, and in some cases it may be necessary to use dosages outside these limits.

Using any of the four methods described above, both a water-soluble compound and water-insoluble compound may be entrapped in one alpha-tocopherol vesicle preparation.

According to the methods described above for the entrapment of water-insoluble compounds using the alpha-tocopherol vesicles of the present invention, it is not required that the vesicles remain intact once a water-insoluble compound partitions into the bilayers. In face, once the compound partitions into the bilayers, the vesicles may be disturbed or disrupted leading to the leakage or release of aqueous entrapped compounds. Although these "leaky" vesicles could be used to deliver the entrapped water-insoluble compound, they should not be used to encapsulate or deliver a water-soluble substance.

According to one embodiment of the present invention, liposomes can be prepared using the tris-salt form of alpha-tocopherol hemisuccinate as follows: about 1 to 400 mg of the tris-salt form of alpha-tocopherol hemisuccinate is added per ml of aqueous buffer containing 0.01 M Tris-HCl, 0.14 M NaCl. The mixture is shaken and a milky suspension of alpha-tocopherol hemisuccinate vesicles forms. The vesicles may be pelleted by centrifugation and washed repeatedly with aqueous buffer. Suspension of alpha-tocopherol hemisuccinate multilamellar vesicles (AHS-MLVs) may be sonicated to form alpha-tocopherol hemisuccinate small unilamellar vesicles (AHS-SUVs). The vesicles are unstable in the presence of divalent cations; i.e., upon exposure to divalent cations the entrapped aqueous compartment and water-soluble compounds are released. Thus, the aqueous medium used in the preparation or during storage of the vesicles should be essentially free of divalent cations.

The compounds which are entrapped according to the method of the present invention may be used in various ways. For example, if the compound is a bioactive agent, the alpha-tocopherol vesicle-entrapped compound may be administered in vivo. This facilitates the in vivo delivery of bioactive agents which are normally insoluble or sparingly soluble in aqueous solutions. Entrapment in vesicles composed of the salt form of organic acid derivatives of alpha-tocopherol enables ease in the administration of such insoluble compounds at a higher dose: volume ratio. In fact, the alpha-tocopherol vesicles of the present invention are particularly advantageously used in vivo because the vesicles may be used to entrap one or more bioactive agents for delivery in vivo. Furthermore, the vesicles of the present invention offer an advantage over conventional lipid vesicles or liposomes when used in vivo because they can be prepared without using organic solvents.

Compounds which are bioactive agents can be entrapped within the alpha-tocopherol vesicles of the present invention. Such compounds include but are not limited to antibacterial compounds such as gentamycin, antiviral agents such as rifampacin, antifungal compounds such as amphoteracin B, anti-parasitic compounds such as antimony derivatives, tumoricidal compounds such as adriamycin, anti-metabolites, peptides, proteins such as albumin, toxins such as diptheriatoxin, enzymes such as catalase, polypeptides such as cyclosporin A, hormones such as estrogen, hormone antagonists, neurotransmitters such as acetylcholine, neurotransmitter antagonists, glycoproteins such as hyaluronic acid, lipoproteins such as alpha-lipoprotein, immunoglobulins such as IgG, immunomodulators such as interferon or interleuken, vasodilators, dyes such as Arsenazo III, radiolabels such as $^{14}C$, radio-opaque compounds such as $^{90}Te$, fluorescent compounds such as carboxy fluorescein, receptor binding molecules such as estrogen receptor protein, anti-inflammatories such as indomethacin, antiglaucoma agents such as pilocarpine, mydriatic compounds, local anesthetics such as lidocaine, narcotics such as codeine, vitamins such as alpha-tocopherol, nucleic acids such as thymine, polynucleotides such as RNA polymers, psychoactive or anxiolytic agents such as diazepam, mono- di- and polysaccharides, etc. A few of the many specific compounds that can be entrapped are pilocarpine, a polypeptide growth hormone such as human growth hormone, bovine growth hormone and porcine growth hormone, indomethacin, diazepam, alphatocopherol itself and tylosin. Antifungal compounds include miconazole, terconazole, econazole, isoconazole, tioconazole, bifonazole, clotrimazole, ketoconazole, butaconazole, itraconazole, oxicanazole, fenticonazole, nystatin, naftifine, amphotericin B, zinoconazole and ciclopirox olamine, preferably miconazole or terconazole. The entrapment of two or more compounds simultaneously may be especially desirable when such compounds produce complementary or synergistic effects. The amounts of drugs administered in liposomes will generally be the same as with the free drug; however, the frequency of dosing may be reduces.

The alpha-tocopherol vesicle-entrapped or -associated agent may be administered in vivo by an suitable route including but not limited to: parenteral inoculation or injection (e.g., intravenous, intrapertioneal, intramuscular, subcutaneous, intra-aural, intra-mammary, and the like), topical application (e.g., on areas such as eyes, skin, in ears or on afflictions such as wounds and burns), and by absorption through epithelial or mucocutaneous linings (e.g., nasal, oral, vaginal, rectal, gastrointestinal mucosa, and the like).

In another example of their use, the alpha-tocopherol vesicle-entrapped compounds may be incorporated into a broad range of materials including but not limited to lipid vesicles or liposomes, gels, oils, emulsions and the like. For instance, the suspension containing the entrapped compound may be added to the aqueous phase as an ingredient in any type of liposome preparation (e.g., phospholipid SPLVs, MPVs, FATMLVs, MLVs, SUVs, LUVs, REVs, and others). This allows the entrapment of the water-insoluble compound in the phospholipid liposomes.

The alpha-tocopherol vesicles of the present invention can be used advantageously in conjunction with vesicles of the salt form of an organic acid derivative of a sterol, such as cholesterol hemisuccinate tris salt vesicles, as described in the copending application entitled "Steroidal Liposomes," Ser. No. 773,429, filed Sept. 10, 1985 and now U.S. Pat. No. 4,891,208 relevent portions of which are incorporated herein by reference. Such steroidal liposomes form bilayer vesicles, may be unilamellar or multilamellar, and can entrap compounds that are bioactive agents.

Generally any sterol which can be modified by the attachment of an organic acid may be used in the practice of the present invention. For example, such sterols include, but are not limited to, cholesterol, vitamin D, phytosterols (including but not limited to sitosterol, campesterol, stigmasterol, and the like), steroid hormones, and the like.

Organic acids which can be used to derivatize the sterols include those that may be used to derivatize alpha-tocopherol, as discussed herein before.

The organic acid can be linked to an hydroxyl group of the sterol via an ester or an ether bond using conventional methods (see, for example, U.S. Pat. No. 3,859,047; U.S. Pat. No. 4,040,784; U.S. Pat. No. 4,042,330; U.S. Pat. No. 4,183,847; and U.S. Pat. No. 4,189,400). The salt forms of the derivatized sterols can be prepared by dissolving both the organic acid derivative of the sterol and the counterion of the salt (e.g., the free base of the salt) in an appropriate volatile solvent, and removing the solvent by evaporation or a similar technique leaving a residue which consists of the salt form of the organic acid derivative of the sterol. Counterions that may be used include, but are not limited to, tris, 2-amino-2-methyl-1,3-propanediol, 2-aminoethanol, bis-tris propane, triethanolamine, and the like to form the corresponding salt. In fact, the free base of an ionizable bioactive agent such as miconazole free base and the like may be used as the counterion. Thus, the bioactive agent can be used as a counterion.

Where an organic acid derivative of a sterol is used in conjunction with alpha-tocopherol in the vesicles of the invention, any ratio of the sterol to alpha-tocopherol may be used from 0:100 to 100:0 mole %.

The alpha-tocopherol vesicles of the present invention can also be used in conjunction with traditional liposomes to solubilize a variety of materials. The material may first be incorporated into alpha-tocopherol vesicles and, thus entrapped, into the liposomes. Alternatively, the material to be solubilized may be present at the onset with all of the materials needed to make both kinds of vesicles.

Other uses, depending upon the particular properties of the preparation, may be envisioned by those skilled in the art. For example, because of their divalent cation sensitivity, the alpha-tocopherol hemisuccinate vesicles of the present invention may be made to entrap indicator dyes which are divalent cation sensitive for use in colorimetric diagnostic assays in vitro.

The following examples are given for purposes of illustration and not by way of limiting the scope of the invention.

EXAMPLE 1

PREPARATION OF THE TRIS SALT OF ALPHA-TOCOPHEROL HEMISUCCINATE

Five grams of alpha-tocopherol hydrogen succinate (Sigma Chemical Co., St. Louis, Mo.) were dissolved in 100 ml of diethyl ether. Tris base (Fisher, Fair Lawn, N.J.) (1.14 g) dissolved in about 5 ml of water was then added in 0.5 ml portions to the ether solution while stirring or shaking. The solution was rotoevaporated to dryness and then further dried under high vacuum, to produce the title compound as a gummy, yellow residue.

EXAMPLE 2

PREPARATION OF THE TRIS SALT OF ALPHA-TOCOPHEROL HEMISUCCINATE

To a solution of 10 g of D-alpha-tocopherol acid succinate in 100 ml of methylene chloride at 25° C. in a 500 ml round bottom flask was added 2.28 g of tris(hydroxymethyl)aminomethane in 3 ml of hot water while vortexing. The reaction mixture was rotated on a rotary evaporator while being kept a 55° C. with a constant temperature bath for 15 minutes.

The solvent was removed under reduced pressure and the resulting material was frozen for 24 hours. The material was removed, ground with a mortar and pestle, and the excess solvent was removed in vacuo for 24 hours. The resulting title compound (4.8 ) was stored in a tightly sealed glass jar and protected from light.

Alternatively, the material was frozen for 48 hours.

In another preparation, the solvent was removed by lyophylization.

EXAMPLE 3

ENTRAPMENT OF ARSENAZO III IN ALPHA-TOCOPHEROL VESICLES

One hundred milligrams of alpha-tocopherol hemisuccinate Tris salt, prepared as described above, were added to 1 ml of a solution containing 0.01 M Tris-HCl, 0.14 M NaCl and 4.5 mM Arsenazo III, all at pH 7.3, and the suspension was subjected to vortex mixing in the presence of 3 mm glass beads. The alpha-tocopherol hemisuccinate Tris salt vesicles that formed were pelleted by centrifugation at 10,000×g for 15 minutes, after which the pellet was washed and recentrifuged 3 times in 10 ml of a solution containing 0.01 M tris-HCl and 0.14 M NaCl, pH 7.3. The resulting pellet was red in color due to the entrapment of Arsenazo III. The degree of entrapment was estimated to be 30 percent.

EXAMPLE 4

SOLUBILIZATION OF PREGNANOLONE

Fifty milligrams of alpha-tocopherol hemisuccinate tris salt, 50 mg of cholesterol hemisuccinate Tris salt and 20 mg of 5 beta-Pregnan-3-ol-20-one (Kabi Vitrum, Stockholm, Sweden) were added to an excess amount of methanol and dried under vacuum in a round bottom flask. A resulting film was then resuspended in 1.0 ml of 10 mM Tris-HCl buffer with 140 mM NaCl, pH 7.4 with shaking in the presence of glass beads until a stiff gel formed. The viscosity of the gel was reduced by extensive sonication in a Branson E-module (40 KHz) 5-gallon water bath sonicator, to yield 0.2–0.4 micron diameter vesicles.

The cholesterol hemisuccinate Tris salt had been prepared as follows. Cholesterol hydrogen succinate (50.3 g, 0.11 moles) from ICN, Cleveland, Ohio, was dissolved in 1.5 liters of diethyl ether. Tris base (12.1 g, 0.1 moles) from Fisher, Fairlawn, N.J., was dissolved in 30 ml of water. The Tris solution was then added to the cholesterol solution, and the resulting solution was rotoevaporated to a milky wet residue. The milky residue was freeze dried for 12 hours, after which the cholesterol hemisuccinate Tris salt product was recrystallized three times from about 5-liter volumes of boiling ethyl acetate.

The boiling ethyl acetate solution was filtered hot and cooled to room temperature. A gel-like cholesterol hemisuccinate Tris salt appeared which was filtered through a 100 ml scintered glass funnel, and the ethyl acetate was removed. Initial removal of the solvent was by squeezing. In another preparation, initial solvent removal was performed by mechanical compression. Further solvent removal was carried out under a 0.1 mm Hg vacuum for 12 hours, at which time a silver-dollar sized 23 g disc of hard, brittle white material was evident.

The white disc was pulverized in a mortar and pestle, and the last traces of ethyl acetate were removed by heating the material to 50° C. and applying a 0.1 mm Hg vacuum. Fifty five milligrams of the resulting powder were suspended in 1.0 m of 0.01 M Tris-HCl buffer with 0.14 M NaCl, pH 7.4. A milky suspension developed which was sonicated in the bath sonicator, to form a clear cholesterol hemisuccinate Tris salt vesicle solution.

EXAMPLE 5

SOLUBILIZATION OF CYCLOSPORIN A

Cyclosporin A (Sandoz, Inc., East Hanover, N.J.), cholesterol hemisuccinate Tris salt and alpha-tocopherol hemisuccinate Tris salt were dissolved in methanol in the relative proportions indicated in Table 1.

Aliquots of the solutions sufficient to make 0.25 ml volumes of the final aqueous suspensions were dried to thin films in 13×100 mm test tubes by placing the tubes in 500 ml round-bottom flasks in the 70° C. water bath and removing the solvent by rotary evaporation. The films thus obtained were rehydrated by the addition of 0.25 ml of 0.01 M Tris-HCl buffer with 0.14 M NaCl, pH 7.3, with vortex mixing of the suspensions in the presence of glass beads.

The presence or absence of Cyclosporin A crystals upon microscopic examination under the various conditions listed in Table 1 was noted, with the results shown in FIG. 1. As shown in FIG. 1, when the concentration of cholesterol hemisuccinate tris salt and/or alpha-tocopherol hemisuccinate tris salt were too low, Cyclosporin A crystals were observed.

Figure 2:
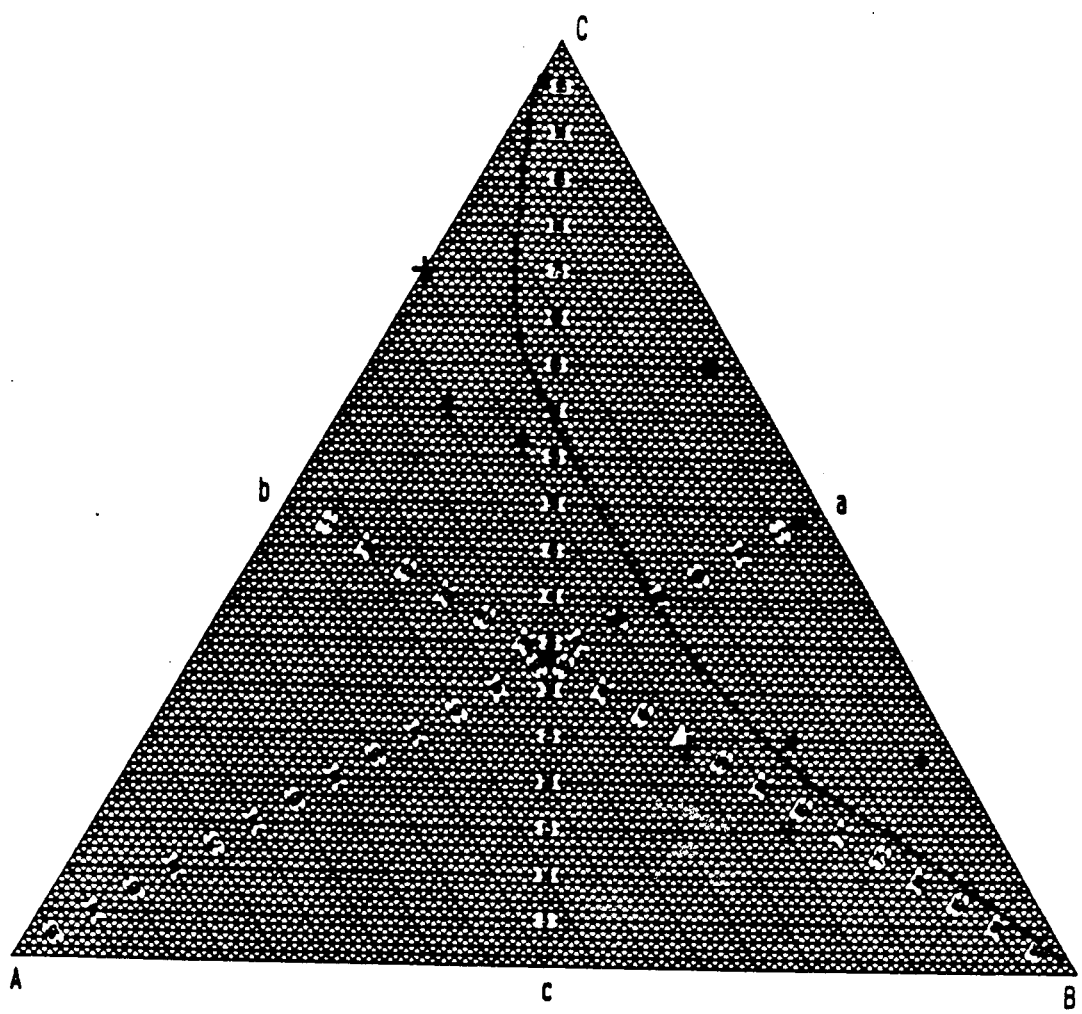

The run was repeated using a 60° C. water bath and the results are shown in FIG. 2.

EXAMPLE 6

SOLUBILIZATION OF MICONAZOLE

Stock solutions of miconazole free base (MCZ), the tris salt of cholesterol hemisuccinate (CHS) and the tris salt of D-alpha-tocopherol hemisuccinate (THS) were prepared as 50 mM solutions in absolute ethanol.

Appropriate volumes of the stock solutions were pipetted to 50 ml round bottom flasks. Each flask contained a total of 0.1 mmoles of material in the relative proportions indicated in Table 2.

The solvent was removed by rotary evaporation at 60° C. The material was then resuspended in 1.0 ml of 0.15 M NaCl with 0.01 M Tris-HCL at pH 7.4.

Figure 3:
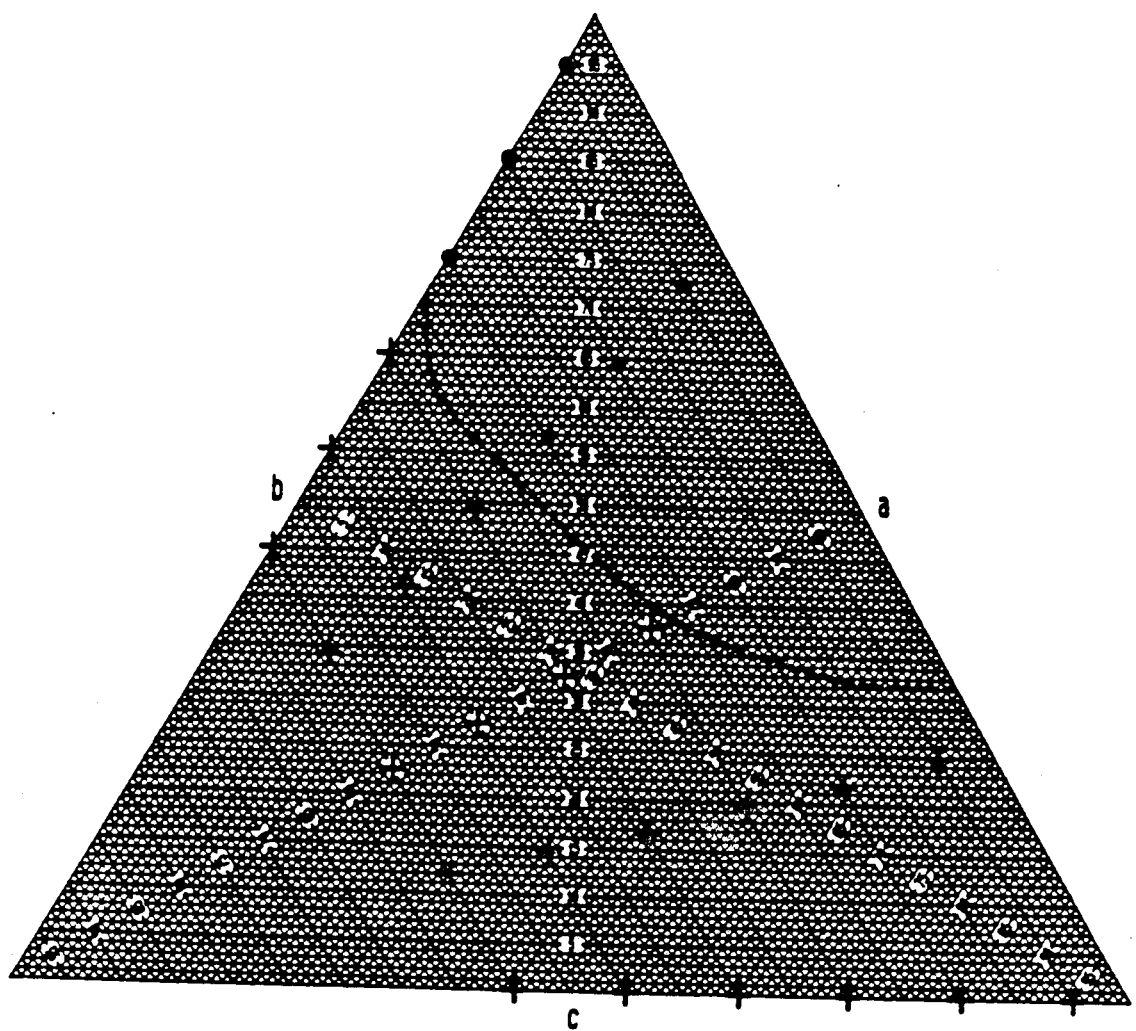
FIG. 3 is a graphical representation of the effects of constituent concentrations on the formation of complex vesicles containing alpha-tocopherol hemisuccinate Tris salt, cholesterol hemisuccinate Tris salt and associated miconazole.

Preparations were examined microscopically for evidence of miconazole crystals and macroscopically for evidence of phase separation over a period of two weeks. Preparations were judged to be acceptable if neither crystals or phase separation were observed (see FIG. 3).

EXAMPLE 7

SUSTAINED DELIVERY OF BOVINE GROWTH HORMONE TO HYPOPHYSECTOMIZED RATS

To demonstrate the solubilizing ability and slow release characteristics of the invention, two types of vesicles were prepared with which bovine growth hormone (BGH) was associated. One type of vesicle contained egg phosphatidyl choline (EPC, or lecithin) and alpha-tocopherol hemisuccinate Tris salt associated with BGH. The other vesicles contained the same components and, additionally, egg phosphatidyl ethanolamine (EPE).

Vesicles lacking EPC were prepared as follows. A solvent phase was prepared by removing the solvent from a chloroform solution containing 400 mg of EPC (Sigma Chemical Co., St. Louis, Mo.) by rotoevaporation at 37° C. The residue was then dissolved in 5 ml of diethyl ether. An aqueous phase containing BGH in association with alpha-tocopherol vesicles was prepared by adding 25 mg of alpha-tocopherol hemisuccinate to 1 ml of 0.01 M Tris-HCl with 0.14 M NaCl, pH 7.4. An opaque suspension developed which was clarified by sonication as described above until an optical density of between 0.3 and 0.6 was obtained at 500 nm. A 0.3 reading is preferable. Twenty-eight milligrams of powdered BGH (Eli Lilly, Indianapolis, Ind.) were added to 0.3 ml of the vesicle preparation by vortexing with brief sonication to disperse the powder. A milky suspension developed which showed no evidence of intact powder. This aqueous phase suspension was added dropwise to the solvent phase, wherein, if undisturbed, the droplets would have sunk to produce an opaque bottom layer.

With the addition of the aqueous phase to the solvent phase, however, the formation of stable plurilamellar vesicles [SPLFs, Lenk et a., U.S. Pat. No. 4,522,803] was promoted by sonicating the aqueous droplets in ether phase while passing a stream of nitrogen over the vessel. The solvent evaporated, leaving a paste which was rehydrated in 10 ml of the above Tris-HCl buffer containing a final concentration of 10 mM $CaCl_2$. The calcium enhanced the tight pelleting of the liposomes upon centrifugation by neutralizing the charge imparted by the alpha-tocopherol hemisuccinate Tris salt. Rehydration was facilitated by gentle vortex mixing.

The resulting SPLVs were pelleted by centrifugation for 10 minutes at 10,000×g, and the pellets from 4 batches were pooled and washed twice more in the Tris-HCl/calcium buffer. The supernatant fluid was decanted, leaving a viscous pellet, approximately 0.5 ml aliquots of which were used for the study below.

Vesicles additionally containing EPE were prepared by combining chloroform solutions containing 1.54 g EPC and 52.8 mg EPE (Avanti Polar Lipids, Inc., Birmingham, Al.) in a round-bottom flask and removing the chloroform by rotoevaporation at 37° C. The resulting dry lipid film was dissolved in 20 ml of diethyl ether, and an aqueous phase containing BGH in association with alpha-tocopherol hemisuccinate Tris salt vesicles was added.

The aqueous phase was prepared by solubilizing 112 mg of BGH in 1.2 ml of 25 mg/ml alpha-tocopherol hemisuccinate Tris salt in 0.01 M Tris-HCl buffer with 0.14 M NaCl, pH 7.4. The alpha-tocopherol suspension had previously been passed through a French Pressure Cell Press (SLM Instruments, Inc., Urbana, Il.) at 40,000 pounds per square inch pressure to produce an optical density at 550 nm of between 0.3 and 0.6.

By adding the aqueous phase to the ether phase with sonication under nitrogen as described above, a viscous SPLV paste was produced that was rehydrated with 20 ml of buffer containing 0.01 M Tris, 0.14 M NaCl and 10 mM CaCl$_2$, pH 7.4. The rehydration was carried out while vortex mixing in the presence of glass beads. The resulting liposomes were washed three times with a total of 20 ml of the above buffer, with centrifugation at 10,000 rpm for 45 minutes in a Backman J2-21 centrifuge, using a JA-14 rotor. Approximately 0.5 ml aliquots of the viscous pellet that resulted were used for the study below.

The slow-release capability of the vesicles was examined in 25-day old female hypophysectomized rats from Charles River Breeding Laboratories, Inc., Wilmington, Ma. The animals were weighed upon arrival and placed on a 5% glucose diet for 2 days, after which they were switched to water and rat chow ad libitum. The animals were weighed at 32 and 39 days of age, and those gaining more than 10 grams weight during the interval were rejected as incompletely hypophysectomized. Groups of eight animals were then injected intramuscularly (I.M.) or subcutaneously (S.C.) with either free BGH or with BGH entrapped in one of the vesicle preparations. Animals receiving free BGH were injected daily S.C., while those receiving vesicle-associated BGH were injected only once on day 0 with about 9.8 mg of associated hormone (assuming 70% association during preparation of the vesicles) for the EPC/EPE formulation or 5.6 mg (assuming 40% association for the EPC formulation), by the routes shown in FIG. 4. Control animals were left untreated. The data represent the average weight change values for the 8 animals of each group.

In FIG. 4, the abbreviations shown are as follows: (1) EPC:EPC/-THS-BGH S.C. means the bovine growth hormone associated with vesicles containing egg phosphatidylcholine and ethanolamine and alpha-tocopherol hemisuccinate Tris salt was administered subcutaneously; (2) EPC/-THS-BGH S.C. means that bovine growth hormone associated with vesicles containing egg phosphatidyl choline and alpha-tocopherol hemisuccinate Tris salt (but lacking egg phosphatidyl ethanolamine) was administered subcutaneously; and (3) EPC/-THS-BGH I.M. is the same as (2) but with intramuscular administration.

As shown in FIG. 4, untreated control animals showed no significant weight gain over the course of the experiment. Strong growth was produced by free BGH, but the administration of the free hormone was carried out daily. Growth stimulation caused by the various associated BGH-vesicle preparations was somewhat lower but remarkable in view of the fact that only a single injection was made of these preparations. The best performance was seen in the case of BGH associated with EPC:EPE/ THS vesicles administered S.C.

EXAMPLE 98

ALPHA-TOCOPHEROL HEMISUCCINATE TRIS SALT ENTRAPMENT OF SOLUTE

Various amounts of the tris salt of D-alpha-tocopherol hemisuccinate ("the Tris salt") powder shown in Table 3 were added in a round bottom flask to 5.0 ml quantities of 0.01 M Tris/0.14 M NaCl buffer (pH 7.4) to which had been added 5 micrometers of $^{51}$Cr. The suspensions were vortexed for two minutes to dissolve the tris salt and allowed to sit undisturbed for two hours, to form MLVs. Meanwhile, Thomas Scientific Spectrapor 12,000 MWCO ¼" dialysis tubing was cut into seven inch lengths and boiled in two changes of distilled water for one hour. The bags were tied at one end, and 1.0 ml from each MLV prep was pipetted into bags. Bags were closed at the top with plastic fasteners and counted for radioactivity i a TMAnalytic model 1191 gamma counter for one minute. Each gab was then dialyzed in 100 ml of Tris/NaCl buffer while stirring. After six hours, the dialysate was changed to fresh buffer. Dialysis continued for twenty hours. Bags were then counted for radioactivity as above and percent $^{51}$Cr entrapped was calculated as follows:

$$\frac{\text{no. averaged counts post-dialysis}}{\text{no. averaged counts pre-dialysis}} \times 100 = \% \ ^{51}\text{Cr. Entrapped}$$

Captured volume (solute) values were calculated as follows: counts from three trials per sample amount of the tris salt were averaged and from the calculated % entrapment (above) and known microliter of sample volume (5.0 ml = 5000 1), the 1/mol $^{51}$Cr per micromole of lipid was calculated as follows:

$$\frac{(\% \ \text{entrapped})(\text{total microliter volume})}{\text{micromoles of the tris salt}}$$

The results are shown in Table 3.

EXAMPLE 9

PILOCARPINE-ALPHA TOCOPHEROL HEMISUCCINATE

Five grams of pilocarpine base were added to a weighed 500 ml round bottom flask and stopper, and the total mass in grams recorded. D-alpha-tocopherol acid succinate (12.75 g, corresponding to a 1:1 M ratio of pilocarpine:D-alpha-tocopherol) was added to the flask and the contents again weighed. Methylene chloride (50 ml) was added and the flask agitated to dissolve the solids and the flask again weighed. The flask was placed on a rotary evaporator in a water bath at 55° C. and rotated for 30 minutes (no vacuum applied). After 30 minutes, the flask and contents were again weighed, then rotary evaporated with vacuum at 55° C. The weight of the flask was recorded every 30 minutes thereafter until two successive weighings were within 0.1 g. The preparation was then cooled to room temperature (25° C.), stoppered, and stored at 4° C.

EXAMPLE 10

PILOCARPINE-ALPHA-TOCOPHEROL HEMISUCCINATE

The materials and procedures of Example 9 were followed using a 5.0 liter round bottom flask and stopper, 30 g of pilocarpine base, 76.5 g of D-alpha-tocopherol acid succinate (corresponding to a 1:1 M ratio of pilocarpine:D-alpha-tocopherol), and 300 ml of methylene chloride.

EXAMPLE 11

PILOCARPINE-ALPHA-TOCOPHEROL HEMISUCCINATE LIPOSOME PREPARATION

The 500 ml round bottom flask containing the product of Example 9 above was placed on a rotary evaporator; with the water bath temperature set at 55° C. The salt was warmed for 30 minutes, then the water bath temperature reduced to 35° C. An aqueous solution of 0.1% (w/v) sorbic acid 0.1% (w/v) sodium EDTA dihydrate (92 ml) was added and the suspension vortically mixed. The final volume was adjusted to 125 ml with additional aqueous phase. The resulting liposomes were processed by CSR (Continuous Size Reduction), a process and device for the continuous processing of large volumes of liposomes to produce size-reduced liposomes having a uniform average mean diameter.

The size reduction device is comprised of: (a) a high pressure piston pump, (b) an in-line filter element having a pre-determined pore size, (c) a reservoir for holding the feed stock (liposome suspension), and (d) a reservoir for collection of the processed feed stock. The system may also include a valving unit to direct the flow of material either back into the feed vessel for recycling or into the process collection vessel. The feed stock may be introduced to the pump by any usual means including but not limited to drawing into the pump head by the piston action of the pump head itself, and/or external pumping of the feed stock by an external device. The pump head then provides the energy for circulation of the feed stock through the filter unit.

In the above example, the liposomes were passed 10 times through a stainless steel filter having a nominal pore size of 500 nm.

The above procedure was also performed using the aqueous phase compositions according to Table 4.

EXAMPLE 12

SIZING STUDY OF PILOCARPINE ALPHA-TOCOPHEROL HEMISUCCINATE VESICLE

The preparation of Example 11 was examined using freeze-fracture electron microscopy. The results show a population of mainly unilamellar liposomes having a size range of about 30–225 nm. Vesicles produced as in example 11 were also measured using quasi-elastic light scattering.

EXAMPLE 13

PILOCARPINE-ALPHA-TOCOPHEROL HEMISUCCINATE

The materials and procedures of Example 11 were followed using the VET400 method (vesicle extrusion technique) of size reduction through two 400 nm pore-size Nucleopore filters. The VET 400 method is described in copending U.S. patent application, Ser. No. 788,017, Cullis et al., entitled "Extrusion Technique for producing Unilamellar Vesicles", filed Oct. 16, 1985, and now abandoned relevant portions of which are incorporated herein by reference.

The above procedure was performed using 0.1% (w/v) sorbic acid with 0.1% (w/v) EDTA as the aqueous phase.

EXAMPLE 14

PILOCARPINE-ALPHA-TOCOPHEROL HEMISUCCINATE COMBINED BATCH LIPOSOME PREPARATION

The materials and procedures of Example 11 were followed and sized batches combined for a total volume of 750 ml. Liposomes were then processed as in example 11.

The above procedure was also performed using the aqueous phase compositions according to Table 6.

EXAMPLE 15

PILOCARPINE-ALPHA-TOCOPHEROL HEMISUCCINATE LIPOSOME PREPARATION

The 5 liter round bottom flask containing the product of Example 10 above was placed on a rotary evaporator; with the water bath temperature set at 55° C. The salt was warmed for 30 minutes, then the water bath temperature was reduced to 35° C. An aqueous solution of 0.01% (w/v) sorbic acid with 0.01% (w/v) disodium EDTA dihydrate (550 ml) was added and the suspension mixed for 1–1.5 hours using an agitator blade. The final volume was adjusted to 750 ml with additional aqueous phase. The resulting liposomes were processed by CSR (Continuous Size Reduction); passing the liposomes 10 times through a stainless steel filter having a nominal pore size of 500 nm.

The above procedure was also performed using the aqueous phase according to Table 7.

EXAMPLE 16

PILOCARPINE-ALPHA-TOCOPHEROL HEMISUCCINATE

The procedure and materials of Example 11 were followed, using a pilocarpiner: D-alpha-tocopherol mole ratio of 1:0.5, corresponding to 1.0 g pilocarpine and 1.28 g D-alpha-tocopherol. Liposomes were formed according to the procedure of Example 12, wherein the aqueous phase added was Water For Injection, USP, to a final concentration of 4% pilocarpine. Results for the viscosity of the above liposome solution are listed in Table 8.

The above procedure was repeated using an aqueous solution of 0.1% (w/v) sorbic acid with 0.1% (w/v) disodium EDTA dihydrate in Water For Injection, USP.

EXAMPLE 17

The procedure and materials of Example 16 were followed, using a pilocarpine:D-alpha-tocopherol mole ratio of 1:2, corresponding to 1.0 g pilocarpine and 5.1 g D-alpha-tocopherol. Liposomes were formed according to the procedures of Example 12, wherein the aqueous phase added was Water for Injection, USP, to a final concentration of 4% pilocarpine. Viscosity results for the above liposome solution are listed in Table 8.

The above procedure was repeated using an aqueous solution of 0.1% (w/v) sorbic acid with 0.1% (w/v) disodium EDTA dihydrate in Water For Injection, USP.

EXAMPLE 18

The procedures and materials of Example 16 were followed, using a pilocarpine:D-alpha-tocopherol mole ratio of 1:4, corresponding to 10 g pilocarpine and 10.2 g D-alpha-tocopherol. Liposomes were formed according to the procedures of example 12, wherein the aqueous phase added was Water For Injection, USP, to a final concentration of 4% pilocarpine. Viscosity results for the above liposome solution are listed in Table 8.

The above procedure was repeated using an aqueous solution of 0.1% (w/v) sorbic acid with 0.1% (w/v) disodium EDTA dihydrate in Water For Injection, USP.

TABLE 1

Solubilization of Cyclosporin A

| Mole Percent | | | |
|---|---|---|---|
| Cyclosporin A | CHS[a] | THS[b] | Total moles/ml[c] |
| 25 | 75 | 0 | 168 |
| 25 | 18.8 | 56.2 | 168 |
| 25 | 37.5 | 37.5 | 168 |
| 25 | 56.2 | 56.2 | 168 |
| 25 | 0 | 75 | 168 |
| 15 | 85 | 0 | 144.5 |
| 15 | 21.3 | 63.7 | 144.5 |
| 15 | 42.5 | 42.5 | 144.5 |
| 15 | 63.7 | 21.3 | 144.5 |
| 15 | 0 | 85 | 144.5 |
| 3 | 97 | 0 | 130 |
| 3 | 24.2 | 72.8 | 130 |
| 3 | 48.5 | 48.5 | 130 |
| 3 | 72.8 | 24.2 | 130 |
| 3 | 0 | 97 | 130 |
| 63 | 63 | 63 | 189 |
| 30 | 60 | 10 | 180 |
| 20 | 20 | 60 | 158 |

[a]CHS is cholesterol hemisuccinate Tris salt.
[b]THS is alpha-tocopherol hemisuccinate Tris salt.
[c]The figures shown are the total number of moles of Cyclosporin A + CHS + THS in the final aqueous solution.

TABLE 2

Proportions (mole percent) of miconazole, cholesterol hemisuccinate (tris salt), and D-alpha-tocopherol hemisuccinate (tris salt) in the preparations (Total micromoles = 0.10)

| Miconazole (Free Base) | Cholesterol Hemisuccinate (Tris Salt) | D-Alpha-Tocopherol Hemisuccinate (Tris Salt) |
|---|---|---|
| 5 | 0 | .95 |
| 5 | .238 | .713 |
| 5 | .475 | .475 |
| 5 | .713 | .713 |
| 5 | .950 | 0 |
| 15 | 0 | 85 |
| 15 | 21.25 | 63.75 |
| 15 | 42.5 | 42.5 |
| 15 | 63.75 | 21.25 |
| 15 | 85 | 0 |
| 25 | 0 | 75 |

TABLE 2-continued

Proportions (mole percent) of miconazole, cholesterol hemisuccinate (tris salt), and D-alpha-tocopherol hemisuccinate (tris salt) in the preparations (Total micromoles = 0.10)

| Miconazole (Free Base) | Cholesterol Hemisuccinate (Tris Salt) | D-Alpha-Tocopherol Hemisuccinate (Tris Salt) |
|---|---|---|
| 25 | 18.7 | 56.3 |
| 25 | 37.5 | 37.5 |
| 25 | 56.3 | 18.7 |
| 25 | 75 | 0 |
| 35 | 0 | 65 |
| 35 | 16.25 | 48.75 |
| 35 | 32.50 | 32.50 |
| 35 | 48.75 | 16.25 |
| 35 | 65 | 0 |
| 45 | 0 | 55 |
| 45 | 13.75 | 41.25 |
| 45 | 27.50 | 27.50 |
| 45 | 41.25 | 13.75 |
| 45 | 55 | 0 |
| 55 | 0 | 45 |
| 55 | 11.25 | 33.75 |
| 55 | 22.50 | 22.50 |
| 55 | 33.75 | 11.25 |
| 55 | 45 | 0 |

TABLE 3

Alpha-Tocopherol Hemisuccinate Tris Salt

| moles | mg | Entrapment Efficiency (%) | /mole |
|---|---|---|---|
| 15.0 | 9.89 | 9.41 ± 0.79 | 31.37 ± 2.63 |
| 40.0 | 26.36 | 12.50 ± 3.36 | 15.63 ± 4.20 |
| 65.8 | 43.37 | 12.84 ± 1.21 | 9.76 ± 0.92 |
| 100.0 | 65.91 | 15.59 ± 4.06 | 7.79 ± 2.03 |
| 175.0 | 115.34 | 17.15 ± 3.49 | 4.90 ± 1.00 |
| 263.2 | 173.48 | 25.01 ± 0.80 | 4.75 ± 0.15 |
| 526.4 | 346.95 | 39.03 ± 0.41 | 3.71 ± 0.04 |
| 658.0 | 433.69 | 50.72 ± 7.57 | 3.85 ± 0.57 |

TABLE 4

| | Aqueous Phase Composition % (w/v) | | | | |
|---|---|---|---|---|---|
| Preparation | BAK | Sorbic Acid | *EDTA | PVA | HPMC |
| 2 | 0.00 | 0.10 | 0.10 | 1.40 | 0.00 |
| 3 | 0.10 | 0.00 | 0.10 | 0.00 | 0.00 |
| 4 | 0.00 | 0.10 | 0.10 | 0.00 | 0.50 |

TABLE 5

MEASUREMENT OF PILOCARPINE - THS VESICLES USING QELS PROCEDURE

| Pilo-THS:Artifical Tears | Diameter (nm) |
|---|---|
| neat | 205 |
| 4:1 | 202 |
| 1:11 | 206 |
| 1:10 | 233 |

TABLE 6

| | Aqueous Phase Composition % (w/v) | | | | |
|---|---|---|---|---|---|
| Preparation | BAK | Sorbic Acid | *EDTA | PVA | HPMC |
| 1 | 0.00 | 0.10 | 0.10 | 0.00 | 0.50 |
| 2 | 0.00 | 0.067 | 0.67 | 0.00 | 0.00 |
| 3 | 0.00 | 0.10 | 0.10 | 1.40 | 0.00 |
| 4 | 0.00 | 0.05 | 0.05 | 0.00 | 0.00 |

TABLE 6-continued

| Preparation | Aqueous Phase Composition % (w/v) | | | | |
|---|---|---|---|---|---|
| | BAK | Sorbic Acid | *EDTA | PVA | HPMC |
| 5 | 0.00 | 0.025 | 0.025 | 0.00 | 0.00 |
| 6 | 0.00 | 0.025 | 0.025 | 0.00 | 0.50 |
| 7 | 0.00 | 0.05 | 0.05 | 0.00 | 0.50 |

TABLE 7

| Preparation | Aqueous Phase Composition % (w/v) | | | | |
|---|---|---|---|---|---|
| | BAK | Sorbic Acid | *EDTA | PVA | HPMC |
| 1 | 0.00 | 0.01 | 0.01 | 0.00 | 0.05 |
| 2 | 0.00 | 0.05 | 0.05 | 1.4 | 0.00 |
| 3 | 0.00 | 0.01 | 0.01 | 1.4 | 0.00 |
| 4 | 0.00 | 0.05 | 0.05 | 0.00 | 0.00 |
| 5 | 0.00 | 0.05 | 0.05 | 0.00 | 0.00 |
| 6 | 0.00 | 0.025 | 0.025 | 0.00 | 0.50 |
| 7 | 0.00 | 0.05 | 0.05 | 0.00 | 0.50 |

TABLE 8

EFFECT OF VARIANCE OF MOLE RATIO OF PILOCARPINE-BASE: D-ALPHA-TOCOPHEROL ON VISCOSITY OF LIPOSOME PREPARATION

| Mole Ratio | Result | |
|---|---|---|
| | WFI | Sorbic Acid EDTA |
| 1:0.5 | viscous | dispersed & turbid |
| 1:1 | dispersed & turbid | dispersed & turbid |
| 1:2 | not dispersible | not dispersible |
| 1:4 | not dispersible | not dispersible |

We claim:

1. A method for administering a compound in vivo, comprising administering to a host the compound entrapped in a vesicle, the bilayers of which comprise a salt form of an organic acid derivative of alpha-tocopherol.

2. The method according to claim 1 in which the vesicles are multilamellar.

3. The method according to claim 1 in which the vesicles are unilamellar.

4. The method according to claim 1 in which the alpha-tocopherol is D-alpha-tocopherol.

5. The method according to claim 1 in which the organic acid derivative is an ester.

6. The method according to claim 1 in which the bilayers comprise a salt form of a carboxylic acid, a dicarboxylic acid or a polycarboxylic acid derivative of alpha-tocopherol.

7. The method according to claim 6 in which the aliphatic carboxylic acid contains up to five carbon atoms.

8. The method according to claim 6 in which the dicarboxylic acid comprises an aliphatic dicarboxylic acid.

9. The method according to claim 8 in which the aliphatic dicarboxylic acid contains up to seven carbon atoms.

10. The method according to claim 9 in which the aliphatic dicarboxylic acid is succinic acid.

11. The method according to claim 2 in which the bilayers comprise a salt form of an hydroxy acid derivative of alpha-tocopherol.

12. The method according to claim 1 in which the bilayers comprise a salt form of an amino acid or a polyamino acid derivative of alpha-tocopherol.

13. The method according to claim 1 in which the bilayers comprise a tris(hydroxymethyl)aminomethane salt form of an organic acid derivative of a alpha-tocopherol.

14. The method according to claim 1 in which the bilayers comprise a 2-amino-2-methyl-1,3-propanediol, a 2-aminoethanol, a bis-tris-propane, or a triethanolamine salt form of an organic acid derivative of alpha-tocopherol.

15. The method according to claim 1 in which the bilayers comprise the tris(hydroxymethyl)aminomethane salt form of a hemisuccinate derivative of alpha-tocopherol.

16. The method according to claim 1 in which the compound comprises a bioactive agent.

17. The method according to claim 16 in which the bioactive agent is selected from the group consisting of antibacterial, antifungal, antiviral and antiparasitic compounds.

18. The method according to claim 17 in which the antibacterial compound is tylosin.

19. The method according to claim 16 in which the antifungal compound is miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole or ciclopirox olamine.

20. The method according to claim 19 in which the antifungal compound is miconazole.

21. The method according to claim 16 in which the bioactive agent is selected from the group consisting of peptides, proteins, glycoproteins and lipoproteins.

22. The method according to claim 21 in which the bioactive agent comprises growth hormone.

23. The method according to claim 22 in which the growth hormone comprises bovine growth hormone.

24. The method according to claim 21 in which the bioactive agent comprises insulin.

25. The method according to claim 16 in which the bioactive agent is selected from the group consisting of dyes, radiolabels, radio-opaque compounds and fluorescent compounds.

26. The method according to claim 16 in which the bioactive agent is selected from the group consisting of anti-inflammatory, antiglaucoma, mydriatic, analgesic and anesthetic compounds.

27. The method according to claim 26 in which the bioactive agent comprises indomethacin.

28. The method according to claim 26 in which the bioactive agent comprises pilocarpine.

29. The method according to claim 16 in which the bioactive agent comprises a narcotic, psychoactive or anxiolytic agent.

30. The method according to claim 29 in which the bioactive agent comprises diazepam.

31. The method according to claim 16 in which the bioactive agent comprises a vitamin.

32. The method according to claim 16 in which the route of administration is parenteral.

33. The method according to claim 16 in which the route of administration is topical.

34. The method according to claim 16 in which the route of administration is intravenous, subcutaneous or intramuscular.

35. The method according to claim 16 in which the route of administration is vaginally.

36. The method according to claim 16 in which the route of administration is orally.

37. Alpha-tocopherol vesicles comprising completely closed bilayers comprising an amino salt form of an organic acid derivative of alpha-tocopherol.

38. The alpha-tocopherol vesicles according to claim 37 in which the vesicles are multilamellar.

39. The alpha-tocopherol vesicles according to claim 37 in which the vesicles are unilamellar.

40. The alpha-tocopherol vesicles according to claim 37 in which the bilayers comprise a tris(hydroxymethyl) aminomethane, 2-amino-2-methyl-1,3-propanediol, a 2-aminoethanol, a bis-tris propane, or a triethanolamine salt form of an organic acid derivative of alpha-tocopherol.

41. The alpha-tocopherol vesicles according to claim 37 where the alpha-tocopherol is D-alpha-tocopherol.

42. The alpha-tocopherol vesicles according to claim 37 in which the salt form of the organic acid derivative is derived from an ionizable bioactive agent.

43. The alpha-tocopherol vesicles according to claim 42 in which the organic acid derivative is the succinic acid hemiester.

44. The alpha-tocopherol vesicles according to claim 42 in which the ionizable bioactive agent comprises an antifungal compound.

45. The alpha-tocopherol vesicles according to claim 44 in which the anitfungal compound is miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole or ciclopirox olamine.

46. The alpha-tocopherol vesicles according to claim 45 in which the antifungal compound is miconazole.

47. The alpha-tocopherol vesicles according to claim 42 in which the ionizable bioactive agents comprise a peptide, protein, glycoprotein or lipoprotein salt form of an organic acid derivative of alpha-tocopherol.

48. The alpha-tocopherol vesicles according to claim 42 in which the ionizable bioactive agents comprise a pilocarpine salt form of an organic acid derivative of alpha-tocopherol.

49. The alpha-tocopherol vesicles according to claim 48 wherein the mole ratio of pilocarpine to alpha-tocopherol is between about 1:0.5 to 1:1.

50. The alpha-tocopherol vesicles according to claim 37 in which the bilayers comprise a salt form of a carboxylic acid, dicarboxylic acid or polycarboxylic acid derivative of alpha-tocopherol.

51. The alpha-tocopherol vesicles according to claim 50 in which the aliphatic carboxylic acid contains up to five carbon atoms.

52. The alpha-tocopherol vesicles according to claim 50 in which the dicarboxylic acid comprises an aliphatic dicarboxylic acid.

53. The alpha-tocopherol vesicles according to claim 52 in which the aliphatic dicarboxylic acid contains up to seven carbon atoms.

54. The alpha-tocopherol vesicles according to claim 53 in which the aliphatic dicarboxylic acid is succinic acid.

55. The alpha-tocopherol vesicles according to claim 37 in which the bilayers comprise a salt form of an hydroxy acid derivative of alpha-tocopherol.

56. The alpha-tocopherol vesicles according to claim 37 in which the bilayers comprise a salt form of an amino acid or a polyamino acid derivative of alpha-tocopherol.

57. The alpha-tocopherol vesicles according to claim 37 in which the bilayers comprise a tris(hydroxymethyl)aminomethane salt form of a hemisuccinate derivative of alpha-tocopherol.

58. The alpha-tocopherol vesicles according to claim 37 which additionally comprise a bioactive agent.

59. The alpha-tocopherol vesicles according to claim 58 in which the bioactive agent is selected from the group consisting of antibacterial, antifungal, antiviral and antiparasitic compounds.

60. Alpha-tocopherol vesicles according to claim 59 in which the antibacterial compound is tylosin.

61. The alpha-tocopherol vesicles according to claim 59 in which the antifungal compound is miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole or ciclopirox olamine.

62. The alpha-tocopherol vesicles according to claim 61 in which the antifungal compound is miconazole.

63. The alpha-tocopherol vesicles according to claim 58 in which the bioactive agent is selected from the group consisting of peptides, proteins, glycoproteins and lipoproteins.

64. The alpha-tocopherol vesicles according to claim 63 in which the bioactive agent comprises growth hormone.

65. The alpha-tocopherol vesicles according to claim 64 in which the growth hormone comprises bovine growth hormone.

66. The alpha-tocopherol vesicles according to claim 63 in which the bioactive agent comprises insulin.

67. The alpha-tocopherol vesicles according to claim 58 in which the bioactive agent is selected from the group consisting of dyes, radiolabels, radio-opaque compounds and fluorescent compounds.

68. The alpha-tocopherol vesicles according to claim 58 in which the bioactive agent is selected from the group consisting of anti-inflammatory, antiglaucoma, mydriatic, analgesic and anesthetic compounds.

69. The alpha-tocopherol vesicles according to claim 68 in which the bioactive agent comprises indomethacin.

70. The alpha-tocopherol vesicles according to claim 68 in which the bioactive agent comprises pilocarpine.

71. The alpha-tocopherol vesicles according to claim 58 in which in which the bioactive agent comprises a narcotic, a psychoactive or anxiolytic agent.

72. The alpha-tocopherol vesicles according to claim 71 in which in which the bioactive agent comprises diazepam.

73. Alpha-tocopherol vesicles according to claim 58 in which the bioactive agent comprises a vitamin.

74. A pharmaceutical composition comprising the vesicles according to claim 37, and a pharmaceutically acceptable carrier or diluent.

75. Alpha-tocopherol vesicles comprising completely closed bilayers comprising a bioactive agent salt form of an organic acid derivative of alpha-tocopherol.

76. The alpha-tocopherol vesicles according to claim 75 additionally comprising a bioactive agent.

77. The alpha-tocopherol vesicles according to claim 75 wherein the bioactive agent comprises pilocarpine.

78. The vesicles of claim 77 wherein the vesicles have a uniform average mean diameter.

79. A composition comprising a tris(hydroxymethyl)aminomethane, a 2-amino-2-methyl-1,3-propane diol, a 2-aminoethanol, a bis-tris-propane, or a triethanolamine salt form of an organic acid derivative of alpha tocopherol, and the bioactive agent pilocarpine, and wherein said composition is a liposome have a uniform average mean diameter.

80. A vesicle comprised of a composition having a salt form of an organic acid derivative of a sterol and a salt form of an organic acid derivative of alpha-tocopherol.

81. A vesicle according to claim 80 additionally comprising a bioactive agent.

82. A vesicle according to claim 81 wherein the bioactive agent is selected from the group consisting of peptides, polypeptides, proteins, glycoproteins and lipoproteins.

83. A vesicle according to claim 82 wherein the polypeptide is an immunosuppressive agent.

84. A vesicle according to claim 82 wherein the polypeptide is cyclosporin A.

85. A vesicle according to claim 81 wherein the bioactive agent is selected from the group consisting of antibacterial, antifungal, antiviral and antiparasitic compounds.

86. A vesicle according to claim 81 wherein the bioactive agent is selected from the group consisting of dyes, radiolabels, radio-opaque compounds and fluorescent compounds.

87. A vesicle according to claim 81 wherein the bioactive agent is selected form the group consisting of anti-inflammatory, antiglaucoma, mydriatic, analgesic, and anesthetic compounds.

88. A vesicle according to claim 81 wherein the bioactive agent comprises a vitamin.

89. A vesicle according to claim 81 wherein the sterol is cholesterol hemisuccinate tris (hydroxymethyl) aminomethane, the alpha-tocopherol is alpha-tocopherol hemisuccinate tris (hydroxymethyl) aminomethane, and wherein the bioactive agent is cyclosporin A.

90. A pharmaceutical composition comprising the vesicle according to claim 89 and a pharmaceutically acceptable carrier or diluent.

91. A vesicle according to claim 80 wherein the sterol is cholesterol hemisuccinate tris (hydroxymethyl) aminomethane and the alpha-tocopherol is alpha-tocopherol hemisuccinate tris (hydroxymethyl)aminomethane.

92. A vesicle according to claim 91 additionally comprising a bioactive agent.

93. A pharmaceutical composition comprising the vesicle according to claim 91 and a pharmaceutically acceptable carrier of diluent.

94. A vesicle according to claim 80 wherein the salt form of the sterol or the alpha-tocopherol is a bioactive agent.

95. A pharmaceutical composition comprising the vesicles of claim 80 and a pharmaceutically acceptable carrier or diluent.

* * * * *

UNITED STATES PATENT AND TRADEMARK OFFICE
CERTIFICATE OF CORRECTION

PATENT NO. : 5,041,278     Page 1 of 2
DATED      : August 20, 1991
INVENTOR(S) : Andrew S. Janoff, et al It is certified that error appears in the above-indentified patent and that said Letters Patent is hereby corrected as shown below:

On the title page:

Section {75} Inventors: insert --Robert L. Suddith, Robbinsville, N.J. --

Column 5, line 16, delete "alpha- tocopherol" and insert therefor --alpha-tocopherol--.

Column 6, line 1, delete "m ore" and insert therefor --more--.

Column 6, line 33, delete "dimethysulfoxide" and insert therefor --dimethysulfomide--.

Column 6, line 60, delete "ay" and insert therefor --may--.

Column 7, line 3, delete "sat" and insert therefor --salt--.

Column 9, line 3, delete "0.1%" and insert therefor --0.01%--.

Column 9, line 50, delete "face," and insert therefor --fact,--.

Column 12, line 46, delete "(4.8 )" and insert therefor --(4.8 g)--.

Column 14, line 63, delete "a.," and insert therefor --al.,--.

Column 16, line 33, delete " i a" and insert therefor --in a--.

Column 17, line 67, delete "example" and insert therefor --Example--.

Column 18, line 26, delete "example" and insert therefor --Example--.

UNITED STATES PATENT AND TRADEMARK OFFICE
CERTIFICATE OF CORRECTION

PATENT NO. : 5,041,278

DATED : August 20, 1991

INVENTOR(S) : Andrew S. Janoff, et al

It is certified that error appears in the above-indentified patent and that said Letters Patent is hereby corrected as shown below:

Column 19, line 19, delete "10 g" and insert therefor --1.0 g--.

Column 21, line 50, Claim 7, delete "cl aim" and insert therefor --claim--.

Column 23, line 27, Claim 45, delete "anitfungal" and insert therefor --antifungal--.

Column 24, line 51, Claim 72, delete "in which in which" and insert therefor --in which--.

Column 25, line 29, Claim 87, delete "form" and insert therefor --from--.

Column 16, line 16, delete "98" and insert ---8---.

Signed and Sealed this

Thirty-first Day of August, 1993

*Attest:*

BRUCE LEHMAN

*Attesting Officer*   Commissioner of Patents and Trademarks